United States Patent [19]

Huber et al.

[11] Patent Number: 4,923,506

[45] Date of Patent: May 8, 1990

[54] POLYHYDROXY POLYMER DELIVERY SYSTEMS

[75] Inventors: Ludwig K. Huber, Wayne; Harold G. Monsimer, E. Norriton, both of Pa.

[73] Assignee: Pennwalt Corporation, Philadelphia, Pa.

[21] Appl. No.: 213,446

[22] Filed: Jun. 28, 1988

Related U.S. Application Data

[63] Continuation of Ser. No. 557,074, Dec. 1, 1983, abandoned.

[51] Int. Cl.$^5$ ................ A01N 33/18; A01N 37/22; A01N 57/04; A01N 57/08

[52] U.S. Cl. .......................... 71/121; 71/87; 71/118; 514/86; 514/89; 514/127; 514/132; 514/144; 514/628; 514/646

[58] Field of Search ............... 71/121, DIG. 1, 87, 71/118; 514/86, 89, 127, 132, 144, 628, 646

[56] References Cited

U.S. PATENT DOCUMENTS

| | | | |
|---|---|---|---|
| 3,672,863 | 6/1972 | Esposito | 71/82 |
| 4,093,440 | 6/1978 | Denninger et al. | 71/65 |
| 4,382,813 | 5/1983 | Shasha | 71/88 |
| 4,439,488 | 3/1984 | Trimnell et al. | 428/402.24 |
| 4,440,746 | 4/1984 | Maglio | 424/78 |
| 4,517,006 | 5/1985 | Drake et al. | 71/64.11 |

FOREIGN PATENT DOCUMENTS

| | | | |
|---|---|---|---|
| 0873311 | 6/1971 | Canada | 71/DIG. 1 |
| 1304891 | 11/1961 | France | 264/4.1 |
| 0081403 | 5/1982 | Japan | 71/120 |

OTHER PUBLICATIONS

Worthy, "Natural Polymers Control Pesticide Release", Chemical and Engineering News, 6/28/1976, p. 18.

*Primary Examiner*—Richard L. Raymond

[57] ABSTRACT

A controlled release composition of biologically active materials is prepared by reacting a biologically active agent, aqueous polyhydroxy polymer, inorganic salt, and optional filler(s), drying the product and then grinding the product to the desire particle size. The product is then used, for example, for controlling pests.

6 Claims, No Drawings

POLYHYDROXY POLYMER DELIVERY SYSTEMS

This application is a continuation of application Ser. No. 557,074, filed Dec. 1, 1983, now abandoned.

BACKGROUND OF THE INVENTION

This invention relates to compositions for controlled release of biologically active materials. More specifically, it relates to polyhydroxy polymer/salt compositions with biologically active materials contained within a matrix.

The compositions of the present invention are particularly useful for the prolonged delivery of herbicides and other pesticides by granular application to the soil. As such they decrease the loss of active ingredients.

It is known that polyhydroxy polymers such as polyvinyl alcohols (PVA) can be coagulated from aqueous systems by the addition of various salts. An application of this fact can be found in French Patent 1,304,891, which describes a process for converting PVA into microcapsules by treating PVA dye emulsions with inorganic sulfates.

U.S. Pat. No. 4,382,813 describes the coagulation or precipitation of an entrapped pesticidal agent by the rapid insolubilization of a starch alkoxide containing material with a bivalent cation selected from the group of calcium, barium, and strontium. These systems are limited to materials having low solubility in water and result in a strongly basic matrix and are not applicable to alkali sensitive materials.

No prior art was found that discloses the present invention.

SUMMARY OF THE INVENTION

The present invention is directed to a granular or powder, slow release (or controlled release) matrix-carried biologically active agent prepared by emulsifying or dispersing a biologically active agent, optionally on a filler/inorganic salt, in an aqueous polyhydroxy polymer system selected from the group consisting of polyvinyl alcohols, unmodified, modified and substituted starches, dextrins, natural gums, cellulose derivatives and mixtures thereof, optionally adding a filler, and/or an inorganic salt while thoroughly mixing, drying the product and grinding the dried product to the desired particle size.

DETAILED DESCRIPTION OF THE INVENTION

The present invention requires a biologically active agent, a water soluble/swellable polyhydroxy polymer, a suited inorganic salt, and optional filler(s). The active ingredient, optionally on a filler/inorganic salt, is emulsified/dispersed in the aqueous polyhydroxy polymer system (solution-gel-paste), the inorganic salt or optional filler is added (if not already added as a component with the active ingredient) and the mixture thoroughly blended. Depending on the amount and type of salt used, three results can take place:

1. Precipitation
2. Additional thickening of the gel
3. Little apparent effect

Each requires somewhat different treatment in order to obtain a product.

If the salt and concentration are such that coagulation of the polyhydroxy polymer results, a distinct aqueous phase develops which is separated by decantation, filtration or centrifugation. The precipitate contains part of the inorganic salt and other materials soluble in the brine, and most of the water insoluble organic materials present in the reaction mixture (solvents, active ingredient, etc.). Obviously, if the absorbing power of the coagulated product exceeds the amount of water present in the reaction mixture, all brine is retained in the coagulate. In either case the residual water is removed by drying at ambient and/or elevated temperature (usually ~ 75° C.). If necessary, the dried product is ground and classified to the desired particle size.

For soil application the preferred range is 14–40 mesh most preferred 24–40 mesh, and for other uses smaller or larger particles may be preferred.

If salts are used at concentrations which do not result in separation of the water, a product can be obtained by drying. During the drying process the salt concentration increases resulting presumably in a gradual coagulation of the polyhydroxy polymer. The dried product is ground and classified to the desired particle size. Compared to the above procedure, this method has the advantage that at least in some cases, higher loads of and/or water soluble active ingredient(s) can be incorporated into the matrix.

In the preparation of the composition of the present invention from commercial starch, first, the starch is heated with hot water to form a thick paste. The paste formation step can be carried out at temperatures of 60–100° C. without special equipment. The ratio of starch to water can be varied from 1:2 to 1:12 without apparent effect on the product. The biological agent to be delivered can be added to the hot paste which is convenient when working with low melting solids or the paste can be cooled to near room temperature where volatile or heat sensitive materials are involved. The biological agent is blended with this paste to form a uniform mixture which, in most cases, can be allowed to stand for some time without separation. Coprecipitation of the matrix is brought about by the addition of the salt. The amount of salt used can be varied from 10 grams to 30 grams per 100 grams of water.

A variety of water soluble/swellable polyhydroxy polymers can be used for the present invention. Included are various polyvinyl alcohols, starches (unmodified, modified and substituted types), dextrins, natural gums, cellulose derivatives, etc.

Examples of the polyhydroxy polymers are the various partially or fully hydrolyzed polyvinyl acetates sold as polyvinyl alcohols in various molecular weight ranges, corn starch, oxidized starch, acid modified starch, hydroxyethyl starch, cyanoethyl starch, gum arabic, methyl cellulose, hydroxyethyl cellulose, hydroxypropyl cellulose, methylhydroxyethyl cellulose, etc.

Examples of the inorganic salts of this invention include primarily water soluble sulfates and phosphates such as various alkaline and alkaline earth sulfates (Na, K, $NH_4$ Li, Mg, Ca), aluminum and mixed alkali/aluminum sulfates, zinc sulfate, ferrous sulfate, and various mono-, di- and tri-basic alkali phosphates, and combinations thereof, including various buffers. The salts can be used as solids or in solution.

With respect to optional fillers, a large variety of powdered or granular materials can be employed. Examples are diatomites, attapulgites, bentonites, talcs, montmorillonites, perlites, vermiculites, corn cob grits, wood flour, lignin sulfonates, etc.

The amounts of the various ingredients in the total formulation can be varied widely, i.e., from 5–95% (by weight) of the polyhydroxy polymer(s), 2–50% of the active ingredient(s), 0–80% of the filler(s), and 5–90% of the salt(s). Preferred ranges are 5–90% of polyhydroxy polymer, 5–35% of active ingredient(s), and 30–80% of filler(s). As indicated earlier, the amount of salt depends strongly on the particular system desired, and its optimum is best determined experimentally.

The matrices of the present invention can be used for the delivery of insecticides, acaricides, herbicides, fungicides, nematocides, bactericides, rodenticides, fumigants, animal repellents, insect repellents, plant growth regulators, fertilizers, pheromones, sex lures, flavors, odors, drugs, diet supplements, and biological insect control agents. Typical insectides are, e.g., methyl parathion, parathion, ethoprop, fonofos, fenitrothion, chlorpyrifos, diazinon, phorate, etc., which can be used undiluted, in the form of suited solutions or emulsifiable concentrates, on fillers or salts, or in combinations. Typical herbicides include endothall, trifluralin, 2,4-D, monuron, dicamba, atrazine, alachlor, butylate and EPTC.

The type of biologically active agent that might be delivered from one of these matrices is limited only by its compatibility with the system. For example, the biologically active agent should not be decomposed by the process, react in such a way as to prevent matrix formation, or be irreversibly bound to the polymer. Water solubility and/or polymer compatibility should be such that the active agent should not be substantially leached into the aqueous phase, in those cases where the matrix material is separated by filtration or decantation.

The pH under which the materials of the present invention are formed can be varied from 3–12 by the selection of appropriate salts. In fact, such systems might be buffered to accommodate highly pH sensitive materials such as natural biological products.

EXAMPLE 1

Five grams of polyvinyl alcohol (marketed by Monsanto Corp. under the trademark Gelvatol 9000) were dissolved in 45 grams of water. To this solution 19.0 grams of methyl parathion-loaded diatomite powder [prepared by soaking 13.5 grams of Celatom MN-39 (Eagle Picher) with 4.5 grams technical methyl parathion in ~40 ml methylene chloride, and removing volatile components at ~50° C./130 mm Hg] were added followed by dropwise addition of 30 grams of 25% $Na_2SO_4$ solution. The mixture was filtered and the filter cake (42.0 grams) was dried for one day at ambient temperature and then for 2½ hours at ~75° C. Finally, the product (24.0 grams) was ground in a blender and classified to yield 14.2 grams of granulate of 14–40 mesh size. The materials contained 12.6% of active ingredient and about 8% of $Na_2SO_4$.

EXAMPLE 2

In a procedure similar to Example 1, a dispersion of 19.0 grams of methyl parathion-loaded diatomite in 50 grams of 10% Gelvatol 9000 solution was treated with 30 grams of 25% $(NH_4)_2SO_4$ solution. The resulting granulate assayed for 11.7% of active ingredient.

EXAMPLE 3

Twenty grams of a 12.5% aqueous solution of Vinol 205 (a PVA marketed by Air Products) were blended with 19.0 grams of chlorpyrifos-loaded calcium sulfate powder [prepared by soaking 15.4 grams of Snow White Filler (United States Gypsum Company) with 3.6 grams of technical chlorpyrifos in about 40 ml methylene chloride and removing volatiles at ~50° C./130 mm Hg]. To this dispersion 2.4 grams of phosphate buffer (prepared by thoroughly grinding together 1.2 grams of $NaH_2PO_4.H_2O$ and 1.2 grams of $Na_2HPO_4$) were added incrementally with stirring. The resulting mixture was dried for one day at ambient temperature and then 2½ hours at ~75° C. Finally the product (24.0 grams) was ground in a blender and classified to yield 13.4 grams of 14–40 mesh granulate which contained 16.1% active ingredient.

EXAMPLE 4

Twenty grams of a 12.5% aqueous solution of Vinol 205 were blended with 9.0 grams of methyl parathion-loaded diatomite granules [prepared by dropwise addition at 5.0 grams of technical methyl parathion to 14.0 grams of Celatom MP-78 (Eagle Picher)]. After thorough soaking, the mixture was treated with incremental amounts of $NaH_2PO_4.2H_2O$. As the amount of phosphate was increased to 3.0 grams the mixture became increasingly thicker and finally broke up into an almost dry granulate. The product was dried for one day at ambient temperature and then 2½ hours at ~75° C. The resulting dry granulate (22.5 grams) was ground in a blender and classified to yield 19.3 grams of granulate of 14–40 mesh size. It analyzed for 19.0% of active ingredient.

EXAMPLE 5

Six grams of technical methyl parathion were blended with 60 grams of a 33% aqueous paste of hydroxyethyl starch [prepared by heating 20.0 grams of Clineo 716D (Clinton Corn Processing Co.) and 40.0 grams water for 15 minutes at 80–90° C., and cooling the mixture to ambient temperature]. Then 8.5 grams of finely ground $Al_2(SO_4)_3.18H_2O$ were added incrementally with stirring. After one hour the coagulated product was separated by filtration and dried for one day at ambient temperature and then 2½ hours at 75° C. The product was ground in a blender and classified to 14–40 mesh size. It analyzed for 11.1% of active ingredient.

An experiment similar to the above was carried out but using only 6.0 grams of $Al_2(SO_4)_3.18H_2O$. Only slight coagulation was indicated. The mixture was dried directly (without filtration) and worked up as above. The resulting granulate analyzed for 14.2% of active ingredient.

EXAMPLE 6

Sixteen grams of chlorpyrifos-loaded calcium sulfate (prepared as described in Example 3) were dispersed in 10.0 grams of a 20% solution of gum arabic in water. The mixture was dried for one day at ambient temperature and then 2½ hours at ~75° C. Subsequently, the product was ground in a blender and classified to a particle size of 14–40 mesh. The resulting granulate contained 15.6% of active ingredient.

EXAMPLE 7

In an experiment similar to Example 6, but substituting 13.3 grams of a 15% aqueous solution of gum ghatti for the gum arabic, a granulate containing 16.3% of active ingredient was obtained.

EXAMPLE 8

In an experiment similar to Example 6, but substituting 10.0 grams of a 20% aqueous solution of oxidized starch (sold under the trademark Clinco 370D by Clinton Corn Processing Company) for the gum arabic, a granulate containing 16.3% of active ingredient was obtained.

EXAMPLE 9

In an experiment similar to Example 6 but substituting 10.0 grams of a 20% aqueous solution of cyanoethyl starch (Clinisize 756B, Clinton Corn Processing Company) for the gum arabic, a granulate containing 16.6% of active ingredient was obtained.

EXAMPLE 10

In an experiment similar to Example 6 but substituting 10.0 grams of a 20% aqueous solution of dextrin (sold under the trademark 700 DEX by Clinton Corn Processing Company) for the gum arabic, a granulate containing 15.7% of active ingredient was obtained.

EXAMPLE 11

In an experiment similar to Example 6 but substituting 10.0 grams of a 20% aqueous solution of hydroxyethyl starch (Clineo 716D) for the gum arabic, a granulate containing 16.3% of active ingredient was obtained.

EXAMPLE 12

A paste formed by heating 16 grams of starch (Corn Products Co.) and 5 grams of Vinol 205 in 100 ml of water at 70–80° C., was blended with 3.2 grams of trifluralin. On the addition and dissolution of 30 grams of anhydrous sodium sulfate, the starch coagulated to give a precipitate which was collected by filtration and dried. The product (27.1 grams) analyzed for 7.6% of trifluralin.

EXAMPLE 13

Using the procedure given in Example 12 but substituting 3 grams of Vinol 425 (Air Products) for the Vinol 205, 5 grams of trifluralin was entrapped in a starch matrix to give 31 grams of product which analyzed for 15.1% of trifluralin.

EXAMPLE 14

Using the procedure given in Example 12 but substituting 20 grams of sodium meta-phosphate for the sodium sulfate, 5 grams of trifluralin was entrapped to give a product which analyzed for 14% of trifluralin.

EXAMPLE 15

A paste was formed by heating 16 grams of starch in 100 ml of water at 70–80° C. This paste was allowed to cool slightly and 4.5 grams of technical chlorpyrifos was blended in until a uniform paste was obtained. On addition and dissolution of 20 grams of anhydrous sodium sulfate the starch coagulated to give a filterable solid. This product (20 grams) was dried, ground and sieved to a uniform particle size. The sample analyzed for 11.6% of chlorpyrifos.

EXAMPLE 16

Using the procedure given in Example 15, 5 grams of methyl parathion was entrapped in a starch matrix to give 20.9 grams of product which analyzed for 11.8% of methyl parathion.

EXAMPLE 17

Using the procedure given in Example 15, 5 grams of diazinon was entrapped in a starch matrix to give 29.2 grams of product which analyzed for 12.2% of diazinon.

EXAMPLE 18

Using the procedure given in Example 15, 5 grams of diazinon was entrapped using 30 grams of sodium sulfate to give 26.9 grams of product which analyzed for of 13.8% diazinon.

EXAMPLE 19

Using the procedure given in Example 15, 5 grams of trifluralin was entrapped to give 35.1 grams of product which analyzed for 13.1% of trifluralin.

EXAMPLE 20

Using the procedure given in Example 15, but substituting magnesium sulfate for the sodium sulfate, 5 grams of diazinon was entrapped to give 24.1 grams of product which analyzed for 15.3% of diazinon.

EXAMPLE 21

Using the procedure given in Example 15 but substituting magnesium sulfate for the sodium sulfate, 5 grams of methyl parathion was entrapped to give 22.4 grams of product which analyzed for 14.0% of methyl parathion.

EXAMPLE 22

Using the procedure given in Example 15 but substituting magnesium sulfate for the sodium sulfate, 5 grams of trifluralin was entrapped to give 25.6 grams of product which analyzed for 14.8% of trifluralin.

EXAMPLE 23

Using the procedure given in Example 15 but substituting sodium meta phosphate for the sodium sulfate, 5 grams of diazinon was entrapped to give 24.8 grams of product which analyzed for 14.5% of diazinon.

EXAMPLE 24

Using the procedure given in Example 15 but substituting sodium meta phosphate for the sodium sulfate, 5 grams of methyl parathion was entrapped to give 21.3 grams of product which analyzed for 14.8% of methyl parathion.

EXAMPLE 25

Using the procedure given in Example 15 but substituting sodium meta phosphate for the sodium sulfate, 5 grams of trifluralin was entrapped to give 23.6 grams of product which analyzed for 16.5% of trifluralin.

EXAMPLE 26

The granular product of Example 1 was tested in a laboratory soil bioassay using three-day old housefly larvae as test organisms. The soil was treated with the granular product; thereafter twenty-five larvae were exposed to the treated soil at intervals of 3, 31, 45 and 59 days; the number of adult flies emerging from the soil was counted. The granular product was used at a rate equivalent to ½ lb. of active ingredient per acre applied in 6' bands spaced 40' apart. The results are recorded in Table 1. Percent killed is the percent reduction in adult houseflies emerging from the soil.

TABLE I

| | % Killed | | | |
| --- | --- | --- | --- | --- |
| | Days | | | |
| | 3 | 31 | 45 | 59 |
| Example 1 | 85 | 71 | 81 | 99 |
| MP-loaded filler | 98 | 56 | 22 | 48 |
| Control | 1 | 4 | 4 | 8 |

EXAMPLE 27

The granular product of Example 2 was tested by the method described in Example 26. For comparison a commercial granular soil insecticide (sold under the trademark Lorsban 15G) was included. The results are recorded in Table II.

TABLE II

| | % Killed | | | |
| --- | --- | --- | --- | --- |
| | Days | | | |
| | 3 | 31 | 45 | 59 |
| Example 2 | 86 | 86 | 58 | 44 |
| Lorsban 15G | 86 | 78 | 63 | 32 |
| Control | 0 | 11 | 4 | 3 |

EXAMPLE 28

The granular products of Example 6–11 were tested by the method described in Example 26. The results are recorded in Table III.

TABLE III

| | % Killed | | | |
| --- | --- | --- | --- | --- |
| | Days | | | |
| | 3 | 31 | 45 | 59 |
| Example 6 | 44 | 93 | 76 | 41 |
| Example 7 | 56 | 74 | 75 | 47 |
| Example 8 | 37 | 89 | 82 | 62 |
| Example 9 | 45 | 86 | 74 | 62 |
| Example 10 | 85 | 86 | 68 | 26 |
| Example 11 | 62 | 84 | 80 | 72 |
| Lorsban 15G | 92 | 69 | 49 | 10 |
| Control | 7 | 0 | 7 | 0 |

EXAMPLE 29

The product of Example 15 was tested by the method described in Example 26. The results are recorded in Table IV.

TABLE IV

| | % Killed | | | | |
| --- | --- | --- | --- | --- | --- |
| | Days | | | | |
| | 7 | 17 | 31 | 45 | 59 |
| Example 15 | 100 | 66 | 67 | 72 | 25 |
| Lorsban 15G | 79 | 76 | 67 | 57 | 45 |
| Control | 1 | 0 | 4 | 14 | — |

What is claimed is:

1. A process for making a controlled release biologically active composition which consists essentially of emulsifying/dispersing a pesticide, optionally on an inert filler, in an aqueous polyhydroxy polymer system wherein said polymer is an unmodified starch, adding a water soluble alkali metal or magnesium and an optional inert filler while thoroughly mixing to precipitate a product, drying the precipitated product, and reducing the product to the desired particle size.

2. A process for making a controlled release biologically active composition which consists essentially of emulsifying/dispersing a pesticide, on or together with a water soluble alkali metal or magnesium sulfate plus an optional inert filler in an aqueous polyhydroxy polymer system wherein the polymer is an unmodified starch, drying the product after precipitation from the emulsion/dispersion, and reducing the product to the desired particle size.

3. A process for making a controlled release biologically active composition consisting essentially of emulsifying/dispersing a pesticide, on or together with a water soluble alkali metal or magnesium sulfate plus an optional inert filler, in an aqueous polyhydroxy polymer system wherein said polymer is an unmodified starch, adding another portion of the water soluble alkali metal or magnesium sulfate and an optional inert filler while thoroughly mixing to thereby precipitate said composition, drying the product, and reducing the product to the desired particle size.

4. A process for preparing a controlled release composition of a pesticide contained in a matrix of a water soluble/swellable polymer system, a water soluble alkali metal or magnesium sulfate and an optional filler(s), said process consisting essentially of precipitating said composition from an aqueous emulsion/dispersion of an essentially water insoluble pesticide in a hydrophilic polymer, wherein said polymer is an unmodified starch, by the addition of a water soluble alkali metal or magnesium sulfate, drying the precipitate, and reducing it to the desired particle size.

5. The composition of claim 4 in which the pesticide is a herbicide.

6. The composition of claim 5 in which the herbicide is a nitro compound.

* * * * *